United States Patent [19]
Anfindsen et al.

[11] Patent Number: 5,420,040
[45] Date of Patent: May 30, 1995

[54] METHOD FOR THE MEASUREMENT OF PRECIPITATION OF ASPHALTENE IN OIL

[75] Inventors: Hilde Anfindsen, Landås; Finn Hallstein Fadnes, Fana; Per Fotland, Bergen, all of Norway

[73] Assignee: Norsk Hydro a.s., Oslo, Norway

[21] Appl. No.: 979,233

[22] Filed: Nov. 20, 1992

[30] Foreign Application Priority Data

Nov. 20, 1991 [NO] Norway ............................. 914533

[51] Int. Cl.$^6$ ............................................. G01N 27/06
[52] U.S. Cl. ................................................ 436/60; 436/2; 436/139; 436/140; 436/150; 73/53.05; 73/53.07
[58] Field of Search ................. 436/2, 60, 139, 140, 436/150; 73/53.05, 53.07

[56] References Cited

U.S. PATENT DOCUMENTS 4,434,233  2/1984  Bzdula ............................. 436/60
5,156,975 10/1992  Nelson ............................ 436/140

FOREIGN PATENT DOCUMENTS 2139766 11/1984 United Kingdom ........ G01N 27/22

OTHER PUBLICATIONS

Biktasheva, A. D. "Rapid method for determining asphaltene content in petroleums." Nefteprom. Delo, Nauch. Tekh. Sb. 1967(5), 29–31.

Neumann, H. J. "Definition and analytical determination of the so-called asphaltenes." Brennst.-Chem. 48(3), 66–9 (1967).

Primary Examiner—David A. Redding
Attorney, Agent, or Firm—Wenderoth, Lind & Ponack

[57] ABSTRACT

The invention provides a method and an apparatus for measuring asphaltene precipitation in a petroleum product. The inventive method quantifies the precipitation by measuring changes in the petroleum product's conductivity or capacitance. The inventive apparatus comprises a measuring cell adapted to be filled with a petroleum product or a solution of the product and a flocculant, together with an instrument electrically coupled to the measuring cell for measuring the product's or solution's conductivity or capacitance.

5 Claims, 6 Drawing Sheets

METHOD FOR THE MEASUREMENT OF PRECIPITATION OF ASPHALTENE IN OIL

BACKGROUND OF THE INVENTION

The present invention relates to a procedure and apparatus for measuring asphaltene precipitation.

Asphaltene is definable as the fraction of an oil which is insoluble in N—$C_5$ and soluble in benzene. The definition is, in other words, operational. There is no stringent physical or chemical definition. The structure of asphaltene monomer varies from oil to oil, but is generally supposed to consist of aromatic macromolecules having a significant content of heteroatoms (N,S,O). The asphaltenes are presumed to exist in solution partially as monomers and partially as colloidal aggregates with a continuous size dispersion.

Experiments show that asphaltenes, either dissolved in an oil or in a precipitate, have a very wide range of sizes. Typical data shows a molecular weight distribution extending from about 1000 to over 200,000.

Precipitated asphaltene is a big problem in connection with exploitation and processing of petroleum products. Asphaltenes are deposited in valves, tubing and process equipment. At worst, these deposits lead to complete blockage and production stoppage, with substantial costs as consequences.

Whether asphaltenes precipitate from a petroleum product, e.g. crude oil, substantially depends upon the oil's pressure, temperature and composition. Problems with asphaltene precipitation are seldom expected. This is because knowledge about asphaltene precipitation is limited and models currently in use are only to some extent predictive.

Neither is there, as of now, on-line equipment for detecting or quantifying asphaltene precipitation. Conventional equipment is only applicable in a laboratory context, and is inapplicable for industrial process-control.

A conventional method uses a source of light in the form of a laser or the like with a light detector. Both are put in an oil sample diluted with a solvent. An injector adds a flocculant (a flocculating agent) to initiate flocculation. The flocculation point (the precipitation point) is determined as the light detector registers a reduction in transmitted light occurring when flocculation occurs. The method determines only the flocculation point (flocculation threshold value) and cannot measure asphaltene precipitate. Besides, the method is not selective and consequently does not indicate if the precipitate is asphaltene or another constituent, like sand, found in the oil.

Another conventional method for detecting the flocculation point for an oil sample is based upon the measurement of the surface tension at the interface between oil and water as a function of added quantities of flocculant. When precipitation occurs, the interfacial surface tension increases and the flocculation point can thereby be determined. However, the quantity of precipitated asphaltene cannot be determined by this method. Also, its accuracy and reproducibility are uncertain. Furthermore, the method is work-intensive and inapplicable for pressure testing.

These last two conditions apply also to a third conventional method, gravimetry, based on standard liquid chemistry. Oil and flocculant are mixed at a desired proportion to precipitate asphaltenes. The precipitate is centrifuged, washed and weighed.

This method is used only to determine the quantity of asphaltene precipitate in an oil sample and cannot give the oil's flocculation point without a series of very detailed and time-consuming gravimetric analyses.

In summary, the conventional methods are only applicable in a laboratory context. Considering this, and the fact that currently there are no predictive models for determining asphaltene precipitation, the inventors decided to develop a method and an apparatus for measuring the precipitation and being used on-line for industrial process control and surveillance.

SUMMARY OF THE INVENTION

All existing measuring methods were analyzed in the context of a literature investigation. Simultaneously, the physical and chemical properties of petroleum products—especially crude oil—were also examined.

Most North Sea oils have a dielectric constant of about $\epsilon = 2$. Pure oils (refined) have a very low conductivity and can be considered to be electrically isolating. Measurements taken by the inventors show that the conducting capacity for crude oil (without gas) is in the area of 1 nS/m, which is also low, but higher than that of refined oil. There seems to be a certain agreement in the literature that the asphaltene molecules carry an electric charge.

With this starting point, the inventors measured crude oil's conducting capacity in order to see if it changed upon precipitation of asphaltenes in the oil. These measurements were taken on crude oil samples with added flocculant (pentane, hexane, and heptane). It was surprisingly found that there was a relationship between conducting capacity and the precipitation.

After these initially promising measurements, a theoretical analysis and further measurements were undertaken to determine whether asphaltene precipitate could be quantified on the basis of the relationship. Equally surprisingly, it was found that the precipitation could be quantified by conductivity measurements.

Thus, the present invention was arrived at in the form of a method and an apparatus which could determine the flocculation point for a petroleum product and the quantity of asphaltene precipitate, and could also be used on-line for surveillance and control of processes at the temperature and pressure conditions of petroleum products.

The invention is a significant technical advance compared with conventional methods and equipment which are useful only in a laboratory context and which generally do not consider the pressure and temperature conditions naturally existing.

The inventive method is characterized by the asphaltene precipitate being quantified by measuring the change in the petroleum product's conducting capacity or capacitance. Further, the inventive apparatus is characterised by a measuring cell adapted to be filled with a petroleum product or a solution thereof and a flocculant, wherein the measuring cell is electrically coupled to an instrument for measuring the liquid's conductivity or capacitance.

BRIEF DESCRIPTION OF THE DRAWINGS

The invention shall be further described in the form of a preferred embodiment, and with reference to the drawings wherein.

DETAILED DESCRIPTION OF THE PREFERRED EMBODIMENTS

Figure 1:
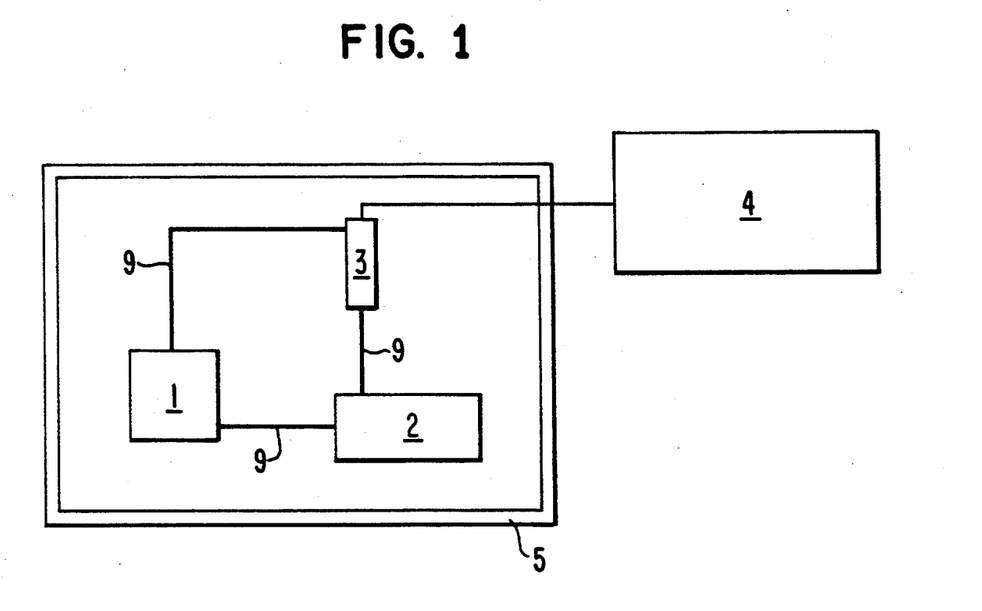
FIG. 1 shows a sketch of an apparatus in accordance with the invention.

As previously stated, FIG. 1 is a sketch of the inventive apparatus. It includes a container or dilution flask 1 for oil, a pump 2, a measuring cell 3 and an impedance meter 4. The container 1, the measuring cell 3 and the pump 2 are coupled together by tubing 9 and are arranged in a heating chamber 5 for temperature control during testing.

The apparatus operates in such a manner that the contents of the container 1 (oil and a flocculant) is pumped via pump 2, through the measuring cell 3 and back to the container 1. The container 1 is large enough to contain both the oil sample and the flocculant so that measurements can be taken over the entire weight fraction interval of the flocculant.

Most commercial conductivity cells are intended for conventional solutions of salts and the like. Geometrically, these are constructed as two plates (electrodes) facing each other at a given distance. Conductance for this set-up is given as:

$$G = \frac{A}{d} \kappa = \frac{l}{k} \cdot \kappa$$

where A is the area of the plates, d is the distance and $\kappa$ is the specific conductivity, or in deference to the correct terminology, the conductivity. k is the cell constant to be determined for each individual cell. In the inventive set-up, the measuring cell's electrodes are coupled to an impedance meter of the type Hewlett Packard HP4192.

Figure 2:
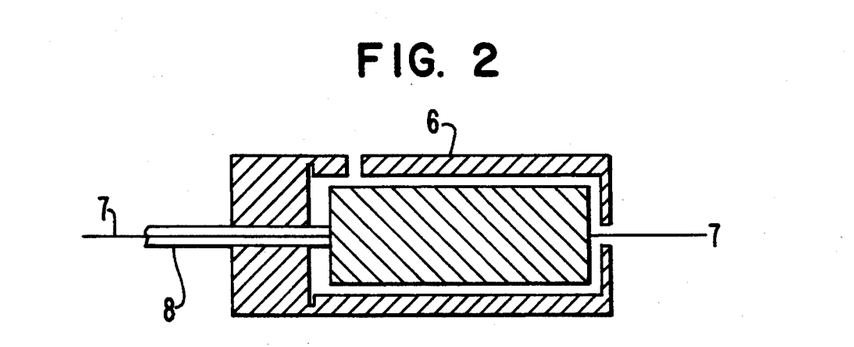
FIG. 2 shows, in enlargement, a sketch of a conductivity cell shown in FIG. 1.

The measuring cell 3 was designed and produced especially for this testing. FIG. 2 shown in detail the measuring cell. It has two concentric cylinders, isolated from each other by a quartz tube 8. These cylinders act as electrodes and the testing is done in the space between them. The distance between the inner and outer electrode can be for example 1 mm. This design provides a large area combined with a small electrode distance. It can be shown that the conductance is given by $$G = \frac{2\pi L}{\ln(r_0/r_i)} \kappa$$

where Ro is the radius of the outer cylinder and $r_i$ is the radius of the inner cylinder. If Ro=7.4 mm, $r_i$=6.5 mm and L=100 mm, then the cell constant=0.21 m$^{-1}$. The conductivity reads off in the area of G=10 nS, and with a solubility of 1 nS; this should make measurements possible. In all measurements, the readouts were registered in the area of G=1–0.5 $\mu$S. Readout errors, due to the solubility, have therefore been from 0.1 to 2%, and reproducibility has been very good. By lowering the cell constant, oils with lower conductivity can be measured. This is done by increasing the length and/or varying the electrode radii while maintaining the electrode distance.

The first cell used for testing was made of brass. It was soon apparent that the brass surface discoloured somewhat, while the measurements were unstable. It was therefore necessary to coat the electrodes with a thin layer of gold.

Testing

Figure 3A:
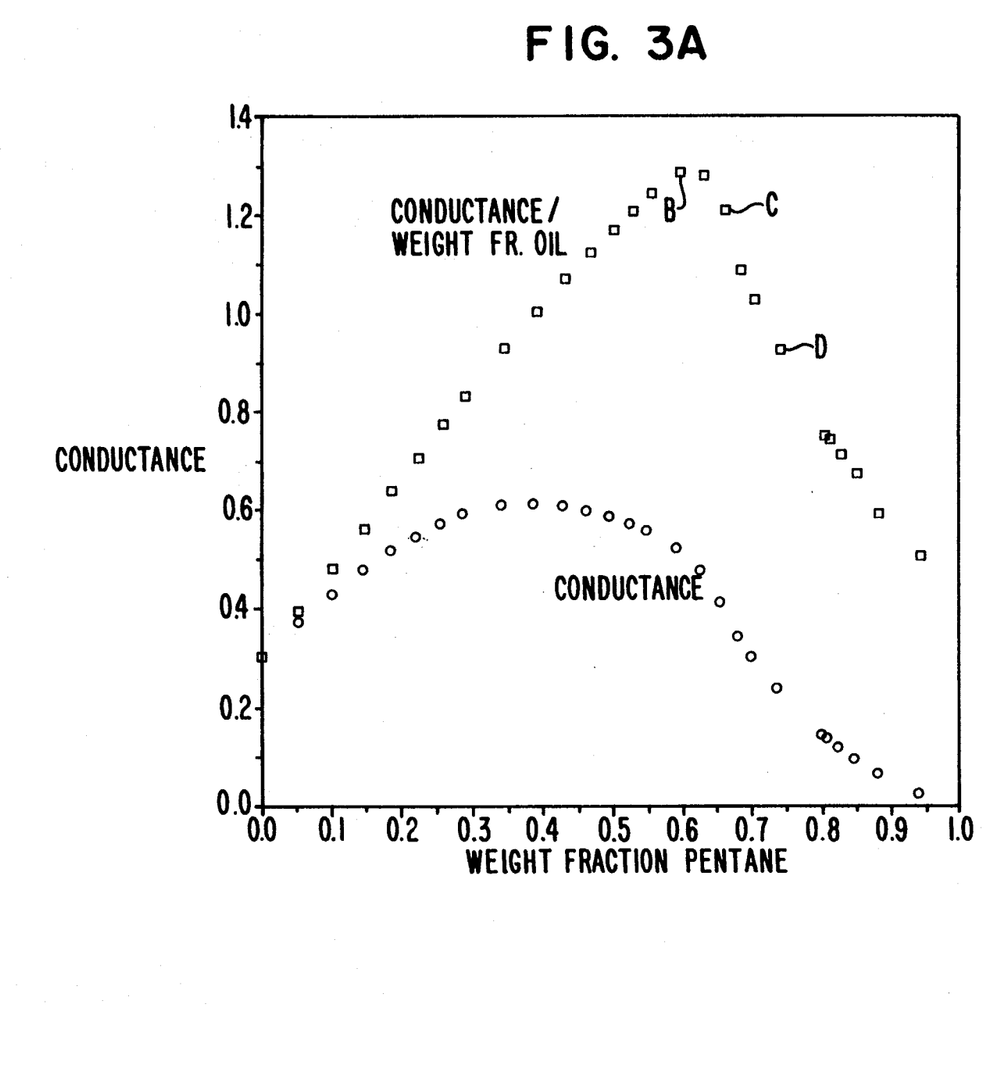
FIG. 3A shows a diagram of results of conductivity measurements as a function of added amount of flocculant.
Figure 3B:
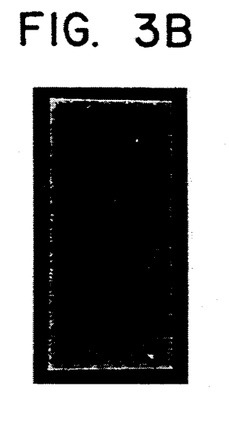
FIGS. 3B–3D are microscopic pictures of solutions at point B–D in FIG. 3A.
Figure 3C:
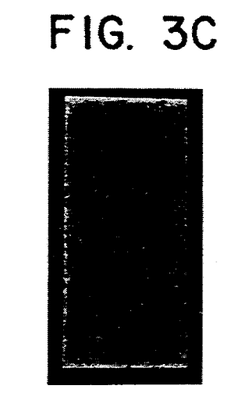
Figure 3D:
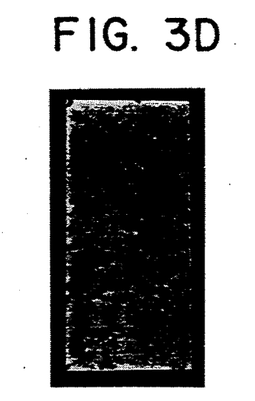

A number of tests were done with the conductivity capacity measurements on crude oil as a function of added amounts of flocculant, pentane, hexane and heptane. A typical curve progression is shown in FIG. 3A together with microscopic pictures of the solutions before and after precipitation in FIGS. 3B—3D. The lower curve in FIG. 3A shows the conductance against the weight percentage of added pentane. An initial climb of conductance can be seen. Thereafter, the curve flattens out towards a maximum and falls off approaching a pure pentane solution. The precipitation point is characterised by a break in the curve at about 60% pentane. At this point, the curvature shifts from initially concave to convex.

The upper curve is derived from the lowers and shows conductance divided by the weight fraction of oil in the sample over the weight fraction of pentane. The background for this data conversion is that the amount of asphaltene in the sample is proportional to the amount of crude oil. Conductivity capacity can be expected to be proportional to the amount of asphaltene present. The concentration dependence emerges more clearly, therefore, where conductance is normalized with amounts of conductive material. In academic literature, the analogous volume is called the molar conductance and is defined as the conductivity divided by the molar concentration. This concept is described in detail in most physical chemistry textbooks. As to the crude oil, there is no possibility of determining the molar concentration (molarity) for asphaltenes; it is therefore necessary to use crude figures like the weight fraction of crude oils which is directly proportional to the weight fraction of asphaltenes.

In the upper curve, the breaking point emerges clearer in the form of a maximum. The precipitation point is therefore characterized by this maximum. Microscopic pictures taken of the sample verify this; precipitation is clearly shown occurring right at this maximum. This has also been verified by gravimetry (jfr. later paragraph). In other words, there is no doubt that this point on the curve is the asphaltenes' precipitation point.

The curve progression (lower curve in FIG. 3A) prior to precipitation is explained easiest with the help of the corresponding viscosity progression, explained in detail in a subsequent paragraph.

The precipitation process itself takes time. If oil and pentane are mixed in a proportion giving precipitation, then it takes time before the precipitation is complete. The kinetics are easily investigated by measuring conductivity as a function of time after mixing. In conventional standard procedures, the solution stands at least 8 hours before further processing.

Measurements show that the kinetics are dependent on the flocculant. This time factor may be important in connection with the production and processing of oil. For example, one could imagine that the conditions for precipitation are present in the local well zone in the reservoir. If precipitation takes some time before being large enough to cause problems, then it is important to be able to predict when and where the problems will arise.

All of the investigated oils have shown the same curve progression. The conclusion drawn from this is that the precipitation point emerges as a break in the conductivity progression measured against an external variable giving precipitation. The term "external variable" denotes, for examples mixture percentages, pressure and temperature. Presently, measurements have only been made against the specified flocculants.

Figure 4:
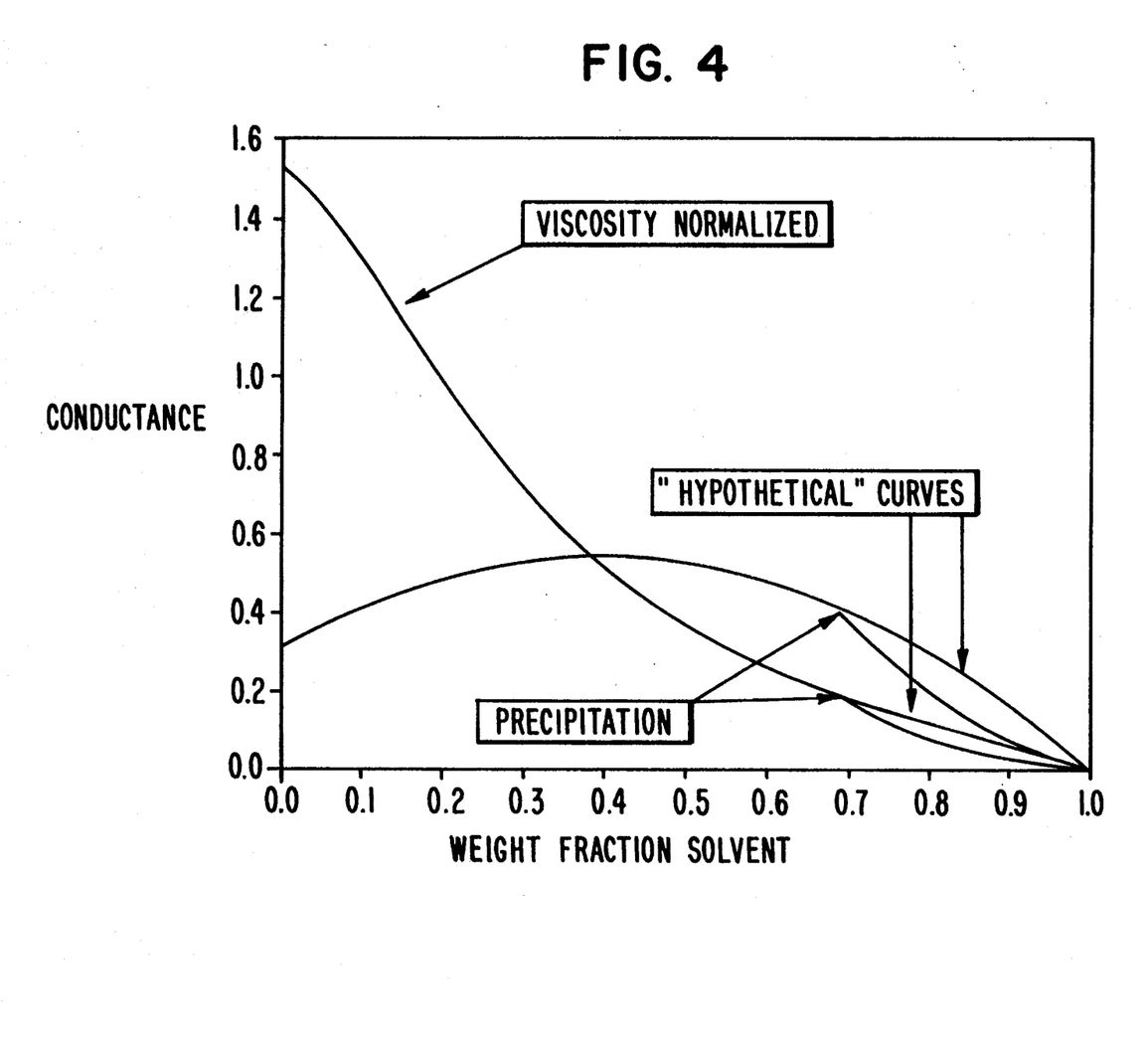
FIG. 4 shows a relationship between measured and viscosity normalised conductivity as a function of a weight fraction of flocculant.

For production and process conditions, it is also important to estimate the amount of precipitant. From the previous paragraph, it can be concluded that the conductivity capacity is proportional to the amount of asphaltenes in solution. The liquid's viscosity changes when adding pentane. Electrical conductive capacity is a property of transport (transport of the charge). In liquids, ions primarily carry this charge by moving in the direction of the field. The liquid's viscosity creates an opposing force of friction. Increasing viscosity therefore leads to decreasing conductivity capacity. This effect is not of interest in this context, and the data is therefore transformed in accordance with:

$$G^n = G \text{ as read off } (\eta \text{ solution}/\eta \text{ flocculant})$$

where $\eta$ solution and $\eta$ flocculant are, respectively, the viscosities of the solution and the pure flocculant. The size of the conductance $G^n$ is now viscosity normalized, i.e. the effect of varying viscosity is eliminated. Such a curve is shown in FIG. 4. It can be seen that the maximum in conductance is no longer found. The conclusion is therefore that this maximum was an effect of the varying viscosity.

Figure 5:
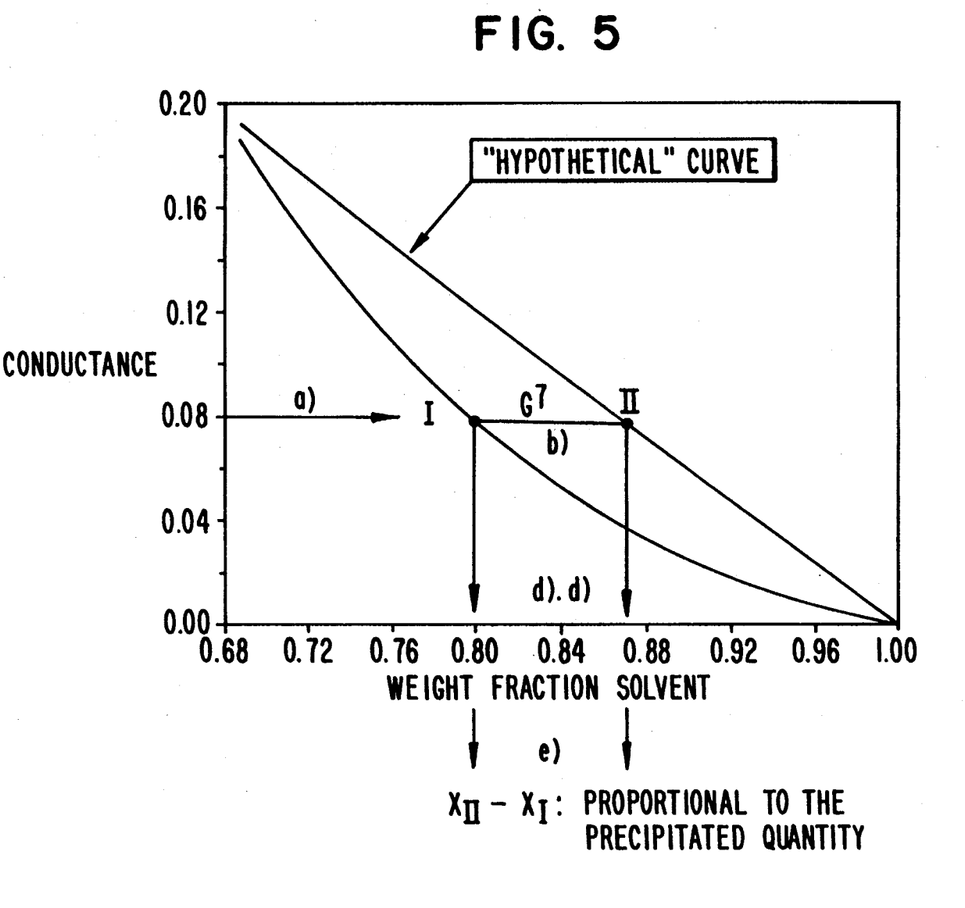
FIG. 5 shows in enlargement a part of the curve shown in FIG. 4.

To quantify the precipitate, a hypothetical curve must be drawn. The conductance progression without precipitation must be estimated. Measurements on oil without precipitation show that the curve will be concave over the entire weight fraction interval. FIG. 4 shows a sketch of the progression of the conductance G with and without precipitation. The drawing also shows the viscosity normalized progression. The interesting part of the curve is the precipitation part. In FIG. 5, this part is enlarged.

To quantify the precipitant, the following premises are used:
a. Given conductance $G^n$.
b. Determine the corresponding concentrations by going into, respectively, the real and the hypothetical curves.
c. These two concentrations of asphaltenes have the same conducting capacity, same viscosity and deviate negligibly as to dielectric constant.
d. It is assumed therefore that they have the same concentration of asphaltenes in solution.
e. The difference between these two concentrations gives therefore the amount of asphaltenes precipitated.

There is an effort to illustrate this sequence of premises in FIG. 5. Upon precipitation, point II in FIG. 5 is displaced to point I, as measured. The displacement along the axis accordingly accounts for the missing material, that is, the precipitation.

It should also be observed that the concentration axis is converted from weight fraction to mass/volume, the physically correct basis for comparison. This is done by measuring the density progression in all mixture proportions between oil and flocculant.

After performing this procedure, the result can be given in terms of chosen units, e.g. the mass of precipitate per total volume or per quantity of crude oil in the sample, etc. The choice of units depends on the context in which the results will be used.

This procedure gives the relative quantities of precipitation. The total amount of asphaltenes in the oil must be determined in relation to the process giving the precipitation. Pentane gives, for example, a greater precipitation than heptane. The asphaltene fraction is precisely defined by the amount of precipitant obtained with a mixture of 1 part oil and 40 parts pentane. The total amount must therefore be seen in context of the flocculant.

Verification of the above-described procedure is done by weighing parallel samples at the given mixture proportions. The samples were subsequently treated in accordance with the standard ASTM method for analysis of asphaltenes. Briefly, this means that they were centrifuged, decanted, the sediment was washed with flocculant, and finally the quantity of precipitate was determined gravimetrically. The gravimetric data, regarded as an answer key, were plotted together with the results from the conductivity procedure. The results showed a very good consistency between the two techniques. It has to be said that the conductivity data is normalised to fit in with the gravimetric analyses only at 100% flocculant.

In this connection it should be noticed that in addition to the conduction measurements, capacitance measurements of petroleum product samples were also taken as a function of added amounts of flocculant. The measurements were taken on "heavy" oil, i.e. oil rich in asphaltenes and wax. As with the conductance measurements, the curve for capacitance measurements showed a break at the flocculation points for the samples. The tests also showed that measuring capacitance instead of conductance can be advantageous if, for example, wax precipitates along with the asphaltenes. The capacitance is, however, sensitive to water, which means that the data can be more difficult to interpret.

Figure 6:
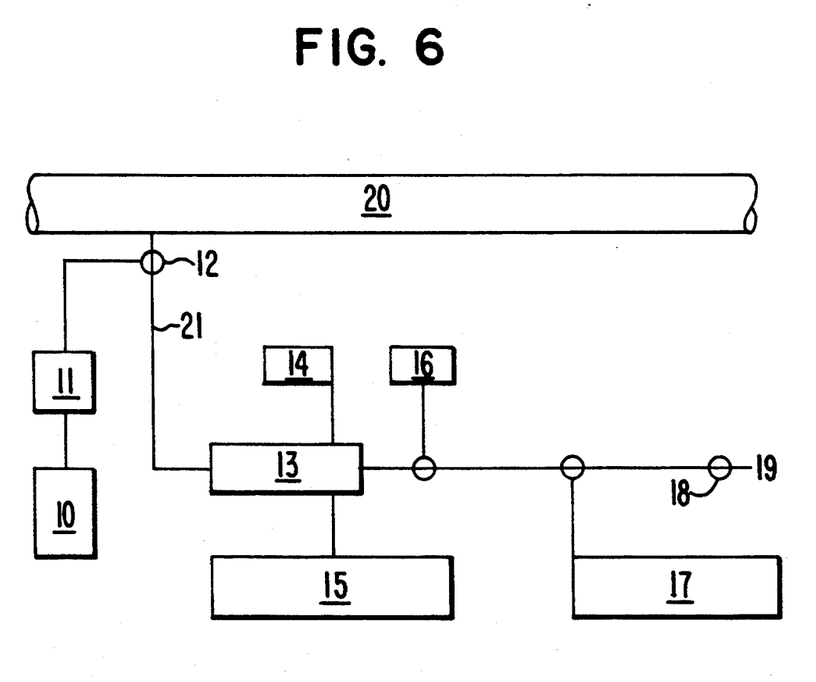
FIG. 6 shows an example of an inventive apparatus as applied in an on-line situation.

The preceding shows and describes a method and an apparatus for measuring asphaltene precipitate in a laboratory context. As previously stated, a substantial advantage of the present invention is that it is useful for on-line measurements, e.g. in connection with exploitation of oil and gas in an offshore context. This is shown in FIG. 6. The apparatus includes a measuring cell 13, an instrument for measuring conductivity (or capacitance) 15, a viscosimeter 17, a thermometer 14, a manometer 16, and a container 10 with a cleaning agent together with a pump. The measuring cell 13 is directly connected to the oil/gas production piping 20 by an appropriately-sized tube 21. The tube 21 can advantageously extend to a closed outlet via a valve 18. Alternatively, the tube 21 can be connected to the production piping 20 such that the oil is conducted back to the piping 20 by means of a pump (not shown). The oil is added to the measuring cell 13 via a two-way valve 12 on the tube 21. Simultaneously, the valve 18 is kept open so that the oil can flow inside. When the temperature in the cell 13, measured with the thermometer 14, is equal to the temperature in the production piping 20, the valve 18 is closed and the pressure is checked with the manometer 16. The pressure reading should be stable during measurements. When pressure and temperature are representative of the oil stream in a production piping, the read-off of conductivity (or capacitance), as well as viscosity, are taken respective by the instruments 15 and 17.

After the measurements are taken, the closed valve 18 is opened and the two-way valve 12 is turned such that it stops the addition of oil, but is open for the addition of cleaning agent from container 10 by means of pump 11.

Measurement of conductivity is corrected for any viscosity changes as previously described, but the viscosity of the flocculant is set as equal to 1 ($\eta$ flocculant=1). The conductivity can, by means of the apparatus, be followed as a function of time. If the conductivity increases over time, then this can indicate that the produced oil is gradually becoming more asphaltene-rich. If, on the other hand, the conductivity decreases over time, then the oil must be checked for possible asphaltene precipitation. The quantity of precipitate can be estimated when a calibration curve has been prepared in advance and shows the viscosity normalized conductance as a function of the amount of asphaltenes for this oil. This correlation can be determined in advance in the laboratory. If one has the calibration curve, then the conductance measurements can be read off and directly converted into the concentration of asphaltenes. Any decline in the conductance can then be stated in terms of the quantity of precipitate.

We claim:

1. A method of detecting asphaltene in a petroleum product, comprising the steps of:

transferring some of the petroleum product to a measuring cell and making an initial measurement of one of the conductivity and capacitance of the petroleum product;

later transferring some of the petroleum product to a measuring cell and making a later measurement of the same one of the conductivity and capacitance of the same petroleum product; and comparing the one of the conductivity and capacitance of the petroleum product for the initial and later measurements to determine if a change in the one of the conductivity and capacitance has taken place.

2. The method of claim 1, and further comprising the step of determining the relative quantity of asphaltene precipitate in the petroleum product by measuring the difference between a weight fraction of flocculant at a factually measured viscosity normalized conductance of the petroleum product and a weight fraction of flocculant at a hypothetical viscosity normalized conductance.

3. The method of claim 1, wherein each of said steps of measuring comprises conducting the petroleum product from production piping to the measuring cell, measuring the one of the conductivity and the capacitance of the petroleum product in the measuring cell and measuring the viscosity of the petroleum product in the measuring cell.

4. The method of claim 3, wherein each of said steps of measuring further comprises measuring the temperature and pressure of the petroleum product in the measuring cell and only measuring the one of the conductivity and the capitance when the temperature and pressure in the measuring cell are representative of the petroleum product in the production piping and the pressure is stable.

5. The method of claim 1, wherein the one of the conductivity and the capacitance is conductivity.

* * * * *